(12) United States Patent
Park et al.

(10) Patent No.: US 8,696,714 B2
(45) Date of Patent: Apr. 15, 2014

(54) INTERVERTEBRAL STABILIZATION DEVICES

(75) Inventors: Jongsoo Park, Los Altos, CA (US); Tzishing Jesse Lim, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1180 days.

(21) Appl. No.: 12/261,929

(22) Filed: Oct. 30, 2008

(65) Prior Publication Data

US 2009/0118766 A1    May 7, 2009

Related U.S. Application Data

(60) Provisional application No. 60/985,097, filed on Nov. 2, 2007.

(51) Int. Cl.
*A61B 17/70*       (2006.01)
(52) U.S. Cl.
USPC ............ 606/279; 606/246; 606/257; 606/258
(58) Field of Classification Search
USPC .................................................. 606/246–279
See application file for complete search history.

(56) References Cited

U.S. PATENT DOCUMENTS

| | | | |
|---|---|---|---|
| 4,611,582 A * | 9/1986 | Duff .............................. | 606/258 |
| 5,102,412 A * | 4/1992 | Rogozinski ................ | 606/86 A |
| 5,167,662 A | 12/1992 | Hayes et al. | |
| 5,180,393 A * | 1/1993 | Commarmond .......... | 623/13.14 |
| 5,267,999 A | 12/1993 | Olerud | |
| 5,352,225 A | 10/1994 | Yuan et al. | |
| 5,395,370 A | 3/1995 | Muller et al. | |
| 5,496,320 A | 3/1996 | Moskovich | |
| 6,117,136 A | 9/2000 | Von Strempel | |
| 6,858,029 B2 * | 2/2005 | Yeh ............................... | 606/276 |
| 7,727,259 B2 * | 6/2010 | Park ............................. | 606/255 |
| 8,075,597 B2 * | 12/2011 | Stahurski et al. ............ | 606/260 |
| 2003/0114852 A1 * | 6/2003 | Biedermann et al. ........... | 606/61 |
| 2004/0215191 A1 * | 10/2004 | Kitchen ......................... | 606/61 |
| 2005/0085815 A1 * | 4/2005 | Harms et al. .................... | 606/61 |
| 2005/0113927 A1 * | 5/2005 | Malek ........................ | 623/17.16 |
| 2005/0154390 A1 * | 7/2005 | Biedermann et al. ........... | 606/61 |
| 2005/0228326 A1 * | 10/2005 | Kalfas et al. .................... | 602/19 |
| 2005/0277932 A1 * | 12/2005 | Farris .............................. | 606/61 |
| 2006/0064090 A1 | 3/2006 | Park | |
| 2006/0084982 A1 | 4/2006 | Kim | |
| 2006/0122620 A1 | 6/2006 | Kim | |
| 2006/0212033 A1 * | 9/2006 | Rothman et al. ................ | 606/61 |
| 2006/0265074 A1 * | 11/2006 | Krishna et al. ............. | 623/17.15 |

(Continued)

OTHER PUBLICATIONS oxforddictionaries.com, definition of "engage" accessed Aug. 15, 2012.*

(Continued)

*Primary Examiner* — Jan Christopher Merene
(74) *Attorney, Agent, or Firm* — Shay Glenn LLP

(57) ABSTRACT

Posterior spinal stabilization devices that engage vertebral structures of at least two verterbrae and increase the stability between the two vertebrae. In some embodiments the stabilization devices engage laminae of at least two vertebrae. The devices can be adapted, however, to engage at least one of a variety of vertebral structures (e.g., spinous process, lamina, transverse process, etc.) of a plurality of vertebrae to decrease vertebral motion between at least two vertebrae.

27 Claims, 25 Drawing Sheets

(56) References Cited

U.S. PATENT DOCUMENTS

| | | |
|---|---|---|
| 2006/0282080 A1* | 12/2006 | Albert et al. .................... 606/61 |
| 2007/0173828 A1* | 7/2007 | Firkins et al. ................... 606/61 |
| 2010/0042156 A1* | 2/2010 | Harms et al. .................. 606/254 |

OTHER PUBLICATIONS

Benzel et al.; Operative stabilization of the posttraumatic thoracic and lumbar spine: a comparative analysis of the harrington distraction rod and the modified weiss spring; Neurosurgery; vol. 19; No. 3; pp. 378-385; Sep. 1986.

Kim et al.: Nitinol spring rod dynamic stabilization system and nitinol memory loops in surgical treatment for lumbar disc disorders: short-term follow up; Neurosurg Focus; 22 (1):E10; pp. 1-9; Jan. 2007.

Kim et al.; (Ch. 37) Shape memory implant (KIMPF-DI fixing) system; Dynamic Reconstruction of the Spine; Thieme Medical Publishers, Inc.; pp. 292-298; 2006.

Kim et al.; (Ch. 43) BioFlex spring rod pedicle screw system; Dynamic Reconstruction of the Spine; Thieme Medical Publishers, Inc.; pp. 340-344; 2006.

Weiss et al.; Biomechanical study in dynamic spondylodesis of the spine; Clinical Orthopaedics and Related Research; No. 103; pp. 199-203: Sep. 1974.

Weiss, Marion; Dynamic spine alloplasty (spring-loading corrective devices) after fracture and spinal cord injury; Clinical Orthopaedics and Related Research; No. 112; pp. 150-158; Oct. 1975.

* cited by examiner

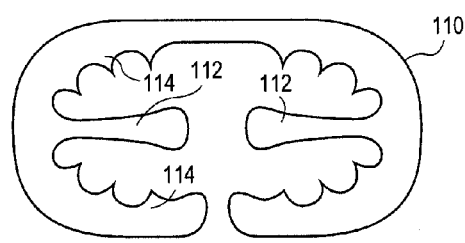
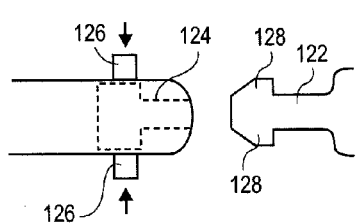
FIG. 14  FIG. 15
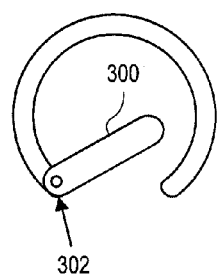
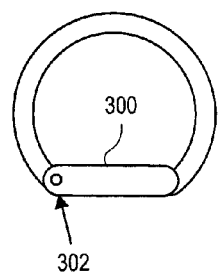
FIG. 16  FIG. 17

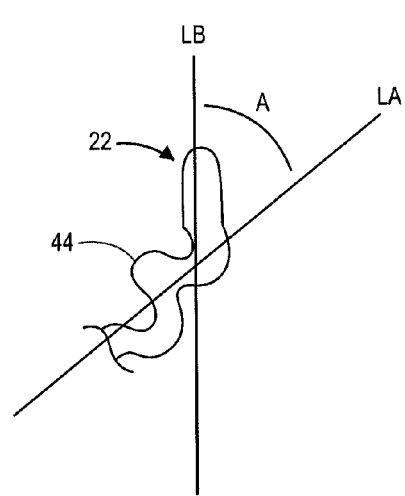
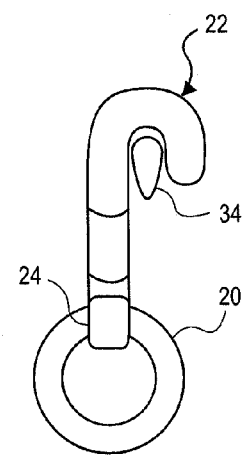
FIG. 21A  FIG. 21B

INTERVERTEBRAL STABILIZATION DEVICES

CROSS-REFERENCE

This application claims the benefit of U.S. Provisional Application No. 60/985,097, filed Nov. 2, 2007, which is incorporated by reference in its entirety as if fully set forth herein.

BACKGROUND OF THE INVENTION

Spinal fusion techniques and devices are well known and operate to essentially lock sections of the vertebral column together. Exemplary fusion devices and techniques include, without limitation, pedicle screws coupled to rigid rods; posterior lumbar interbody fusion (PLIF), anterior lumbar interbody fusion (ALIF); and transforaminal lumbar interbody fusion (TLIF).

Many posterior dynamic stabilization devices are also known. While posterior dynamic stabilization devices do not fuse section of the vertebral column together, they create more stable movement between vertebrae, allow for controlled movement of the spine, and/or allow for more normal movement of the spine. Interspinous process spacers can be considered one subcategory of posterior dynamic stabilization devices, and include, for example, the X STOP®, the Wallis® Posterior Dynamic Stabilization System, and the DIAM™ Spinal Stabilization System.

The KIMPF-DI Fixing (CJSC KIMPF Company, Moscow, Russia) shape memory implant system includes a loop fixing device (Davydov shape memory loop) which comprises two ends which engage lamina of adjacent vertebrae. This device is described in more detail in Kim, Y. & Zhang, H. (2006). Shape Memory Implant (KIMPF-DI Fixing) System. D. H. Kim, F. P. Cammisa, & R. G. Fessler (Eds.) *Dynamic Reconstruction of the Spine* (pp. 292-298). New York: Thieme Medical Publishers, Inc, which is incorporated herein by reference. The device is made of a shape memory material which has a first configuration and a second memory configuration. The Davydov shape memory loop device does not, however, allow for engagement to multiple vertebral structures—such as a lamina and a spinous process. Additional shortcomings of this device are discussed herein below. There remains a need for improved spinal stabilization devices.

SUMMARY OF THE INVENTION

One embodiment of the invention is a vertebral stabilization device. The device includes a first arm, wherein the first arm includes a first engaging end adapted to engage a first vertebral structure of a first vertebra. The first arm also includes a first coupling end and a first length adjustment element. The first length adjustment element has a first configuration with a first length and a second configuration with a second length different than the first length. The device also includes a second arm where the second arm includes a second engaging end adapted to engage a second vertebral structure of a second vertebra and a second coupling end. The device also includes a coupling element engaged with the first coupling end and the second coupling end.

In some embodiments the second arm further comprises a second length adjustment element, the second length adjustment element having a first configuration with a first length and a second configuration with a second length, wherein the second length of the second length adjustment element is different than the first length of the second length adjustment element.

In some embodiments the first engaging end comprises a hook element adapted to hook onto the first vertebral structure.

In some embodiments the first length adjustment element is made of an elastic material such as a shape memory material. In some embodiments at least an entire arm is made of a shape memory material. The first length adjustment element can comprise at least one curved portion with a first radius of curvature in the first configuration and a second radius of curvature in the second configuration, wherein the second radius of curvature is less than the first radius of curvature.

In some embodiments the first coupling end has an annular configuration. The coupling element can have a substantially annular configuration such that the first coupling end and the coupling element engage one another in a chain-like manner.

In some embodiments the device also includes a third arm with a third engaging end which is adapted to engage a third vertebral structure of the first vertebra, wherein the first vertebral structure and the third vertebral structure are different structures. The third arm also includes a third coupling end engaged with the coupling element.

In some embodiments the coupling element has a substantially annular configuration with a first end and a second end, wherein the first end and the second end define a discontinuity in the substantially annular configuration.

In some embodiments the coupling element comprises at least one arm stabilizing element, wherein the at least one arm stabilizing element is shaped to mate with one of the first coupling end and the second coupling end to at least partially constrain the first coupling end or the second coupling end within the coupling element.

In some embodiments the device also includes a third arm with a third engaging end and a third coupling end, and a fourth arm with a fourth engaging end and a fourth coupling end, wherein the third coupling end and the fourth coupling end are engaged with the coupling element. The first and second arms are adapted to engage the coupling element such that they are disposed on one side of the midline of the spine, and wherein the third and fourth arms are adapted to engage the coupling element such that they are disposed on the other side of the midline of the spine. The first engaging end, the second engaging end, the third engaging end, and the fourth engaging end can each include a hook-shaped element adapted to hook onto a lamina.

In some embodiments the device includes a third arm with a coupling end engaging the coupling element and a second end fixedly coupled to a sacral anchor.

One aspect of the invention is a method of stabilizing at least two vertebrae. The method includes engaging a first end of a first elongate member with a lamina of a first vertebra, engaging a first end of a second elongate member with a lamina of a second vertebra, engaging a second end of the first elongate member and a second end of the second elongate member with a coupling element. The method also includes positioning the coupling element in a position inferior to the lamina of the first vertebra and superior to the lamina of the second vertebra, and reducing the length of at least one of the first elongate member and the second elongate member, thereby increasing the stability of the first vertebra relative to the second vertebra.

In some embodiments reducing the length of at least one of the first elongate member and the second elongate member comprises reducing the length of the first elongate member and the second elongate member.

In some embodiments reducing the length of at least one of the first elongate member and the second elongate member comprises changing the configuration of at least one of the first elongate member and the second elongate member from a first configuration with a first length to a second memory configuration with a second length, wherein the second length is shorter than the first length.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 14 shows an alternative coupling element.

FIG. 15 shows a coupling element with a reversible lock to lock two ends of the coupling element.

FIGS. 16 and 17 show a coupling element comprising a door in open and closed positions.

FIGS. 21a and 21b show a plane of an arm engaging end at an angle to the longitudinal axis of the arm body.

DETAILED DESCRIPTION OF THE INVENTION

The invention generally describes spinal stabilization devices and their methods of use. "Stabilization" and "stabilizing" (or any derivatives thereof) as used herein include, but are not limited to, increasing the stability between at least two vertebrae (decreasing relative movement therebetween), as well as fusing or substantially fusing at least two vertebrae together.

In general, the invention relates to posterior spinal stabilization devices that engage vertebral structures of at least two verterbrae and increase the stability between the two vertebrae. In some embodiments the stabilization device engages laminae of at least two vertebrae to stabilize the motion between at least the two vertebrae. The device is, however, adapted to be able to engage at least one of a variety of vertebral structures (e.g., spinous process, lamina, transverse process, etc.) of a plurality of vertebrae to decrease vertebral motion between at least two vertebrae.

Figure 1:
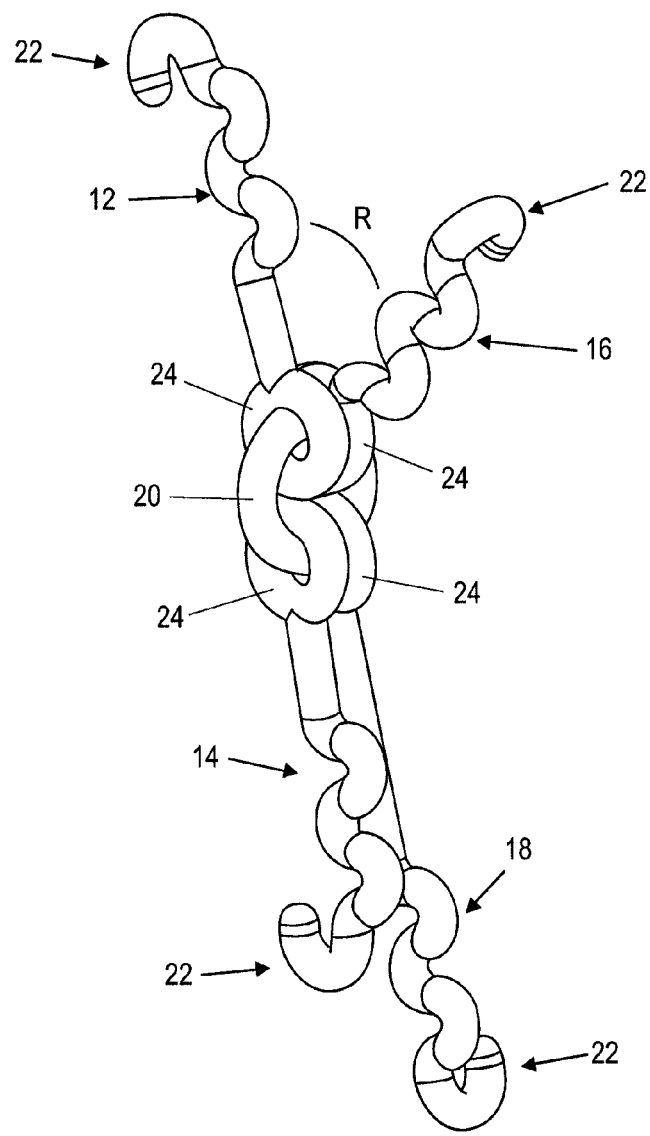
FIG. 1 illustrates an embodiment of a spinal stabilization device.
Figure 2:
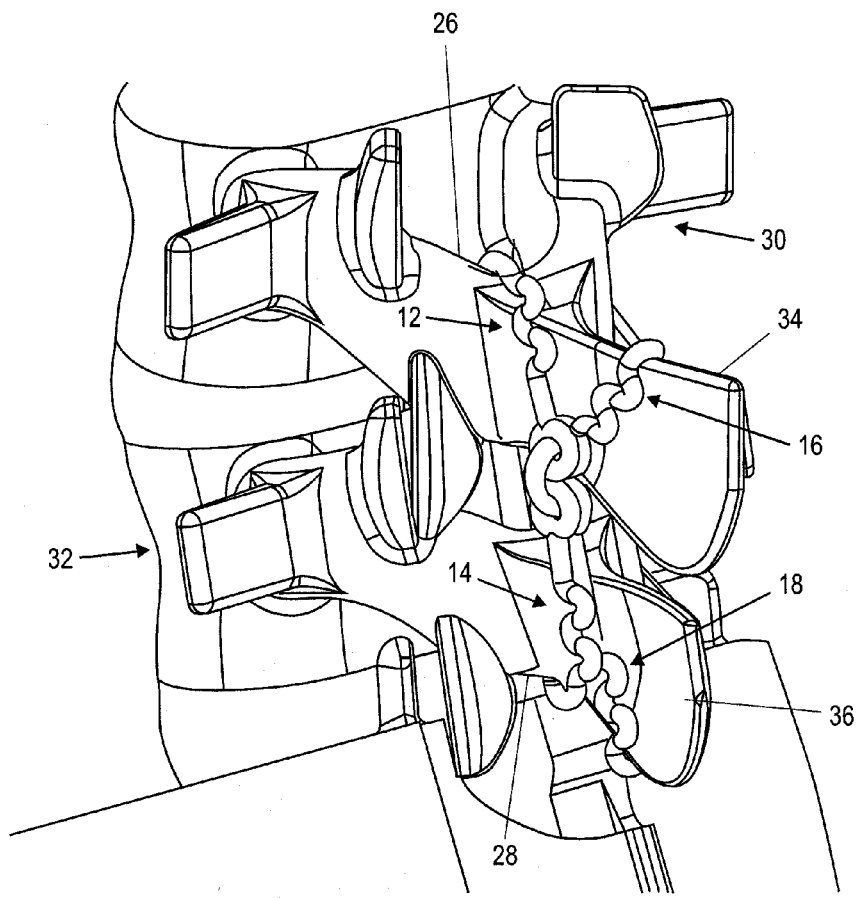
FIG. 2 shows an embodiment of a spinal stabilization device engaging adjacent vertebrae.

FIGS. 1 and 2 show a first embodiment of a spinal stabilization device (vertebrae not shown in FIG. 1). The stabilization device includes a plurality of arms 12, 14, 16, and 18, each separately engaged with coupling element 20. The arms and the coupling element (or coupling member as it may be referred to herein) are coupled together such that they do not disengage from one another without mechanical failure of the coupling element or the arm, or without being actuated by a user (e.g., physician). Each of the arms is shown linkingly engaged with the coupling element, such that the arms and the coupling element have a chain-like engagement.

Each of the arms 12, 14, 16, and 18 are shown with an engaging end 22 adapted to engage a portion of a vertebra and a coupling end 24 adapted to engage coupling element 20. The engaging ends are adapted to engage and generally anchor onto, or grab, a vertebral structure. The engaging ends may have additional anchoring elements such as barbs (not shown) which allow the engaging ends to more securely engage the vertebral structure. As shown, only one end of each arm (the engaging end) is adapted to engage a vertebral structure, whereas the other end of the arm (the coupling end) is adapted to couple to the coupling element. Both ends of the arms are not adapted to couple to a vertebral structure.

In FIG. 2, arms 12 and 14 are shown engaging laminae 26 and 28, respectively, of two adjacent vertebrae 30 and 32. The engaging ends of arms 16 and 18 are engaging the spinous processes 34 and 36 of vertebrae 30 and 32, respectively. The engaging end of arms 16 is shown engaging a superior portion of spinous process 34, while the engaging end of arm 18 is shown engaging an inferior portion of spinous process 36. In FIG. 2, none of the bone of vertebrae 30 and 32 has been removed prior to implanting the spinal stabilization device.

Figure 3A:
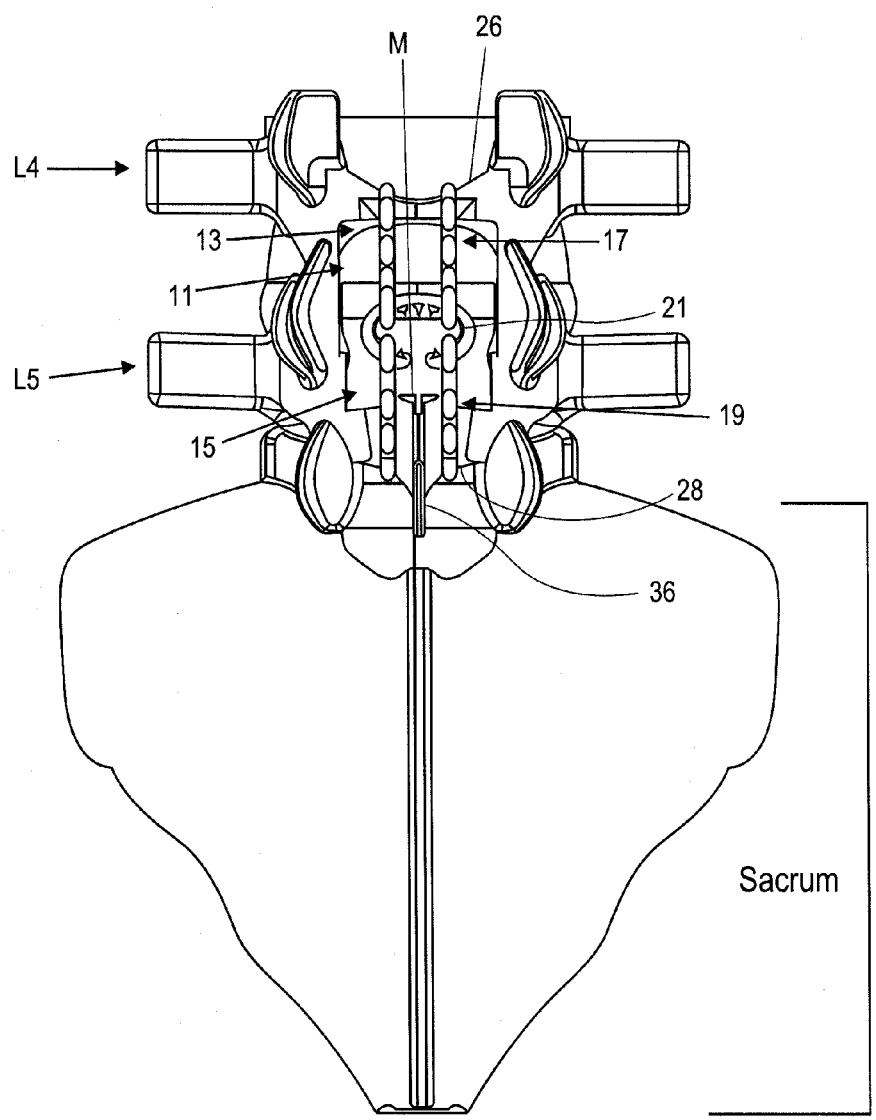
FIGS. 3a-3c show an embodiment of a spinal stabilization device engaging laminae of adjacent vertebrae.
Figure 3B:
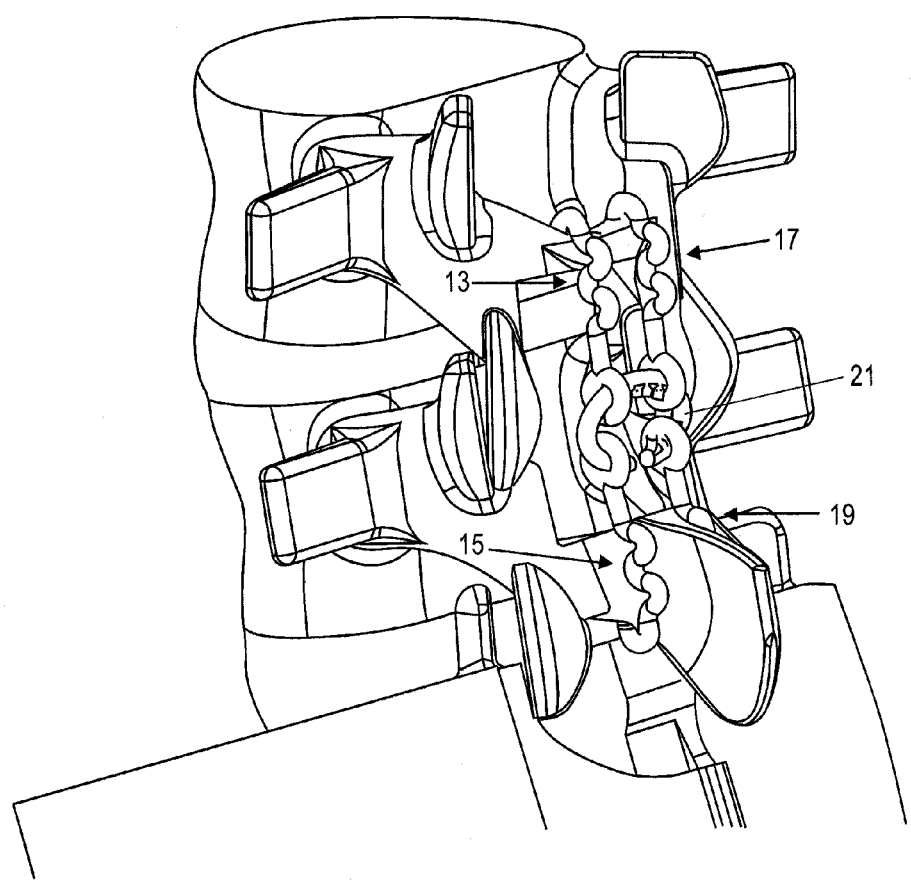
Figure 3C:
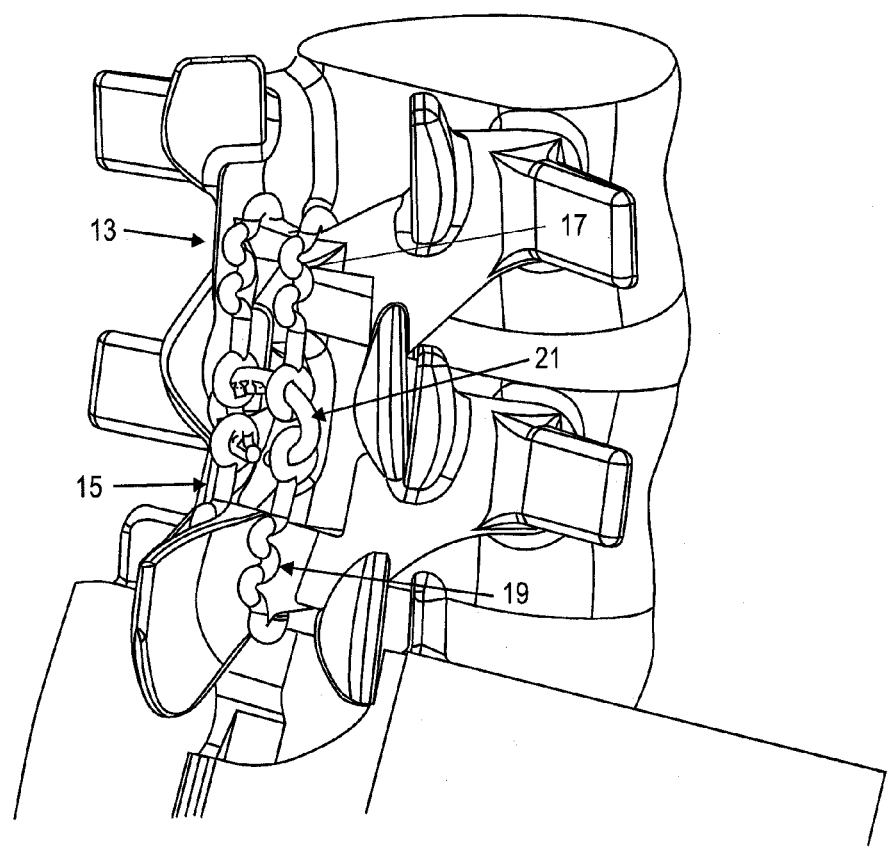

FIGS. 3a-3c show different views of an embodiment of stabilization device 11 comprising four arms 13, 15, 17, 19, and coupling element 21. The engaging ends of arms 13 and 17 are adapted to engage lamina 26 of the L4 vertebra. The engaging ends of arms 15 and 19 are adapted to engage lamina 28 of the L5 vertebrae. The device is shown implanted after a laminectomy has been performed on the L4 vertebra. The device can be implanted, however, without performing a laminectomy such that coupling element 21 would be disposed between the two spinous processes of the L4 and L5 vertebrae (disposed inferior relative to one and superior relative to the other). Arms 13 and 15 are shown on one side of the midline "M", while arms 17 and 19 are shown on the other side of the midline. Coupling element 21 is disposed substantially symmetrically about the midline "M" (i.e., the portions of coupling element 21 on each side of the midline are mirror images of each other).

Figure 4A:
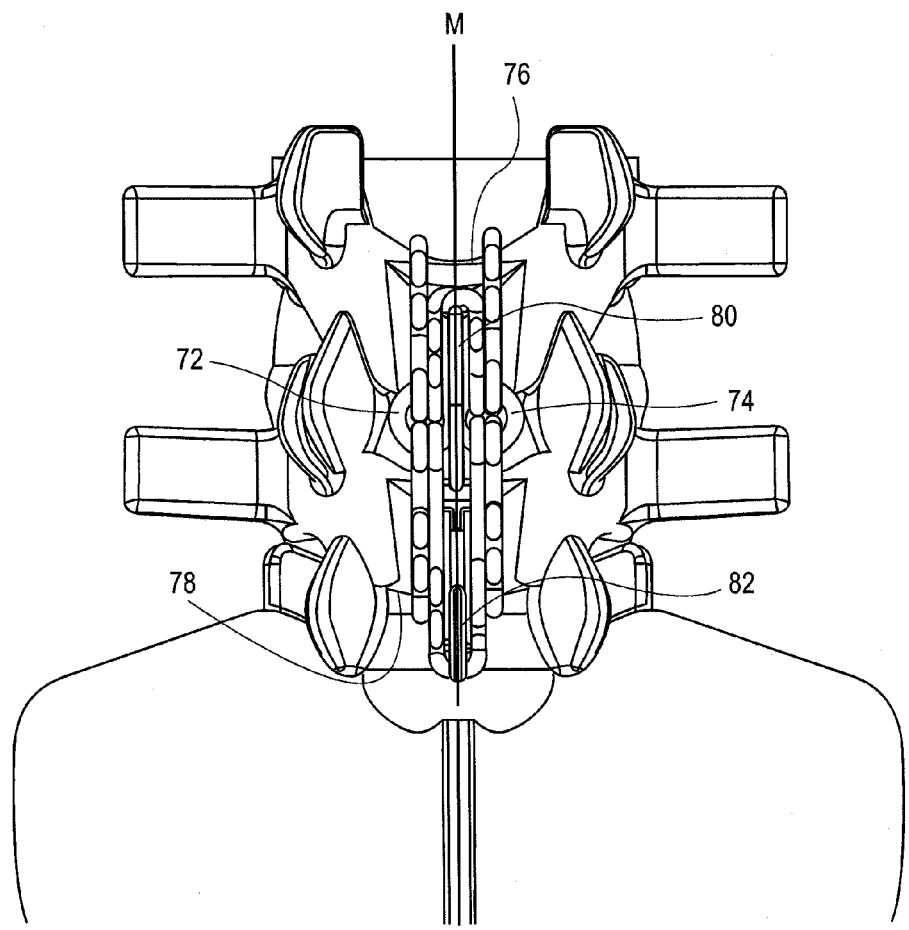
FIGS. 4a-4c show an embodiment of a spinal stabilization device engaging laminae and spinous processes of adjacent vertebrae.
Figure 4B:
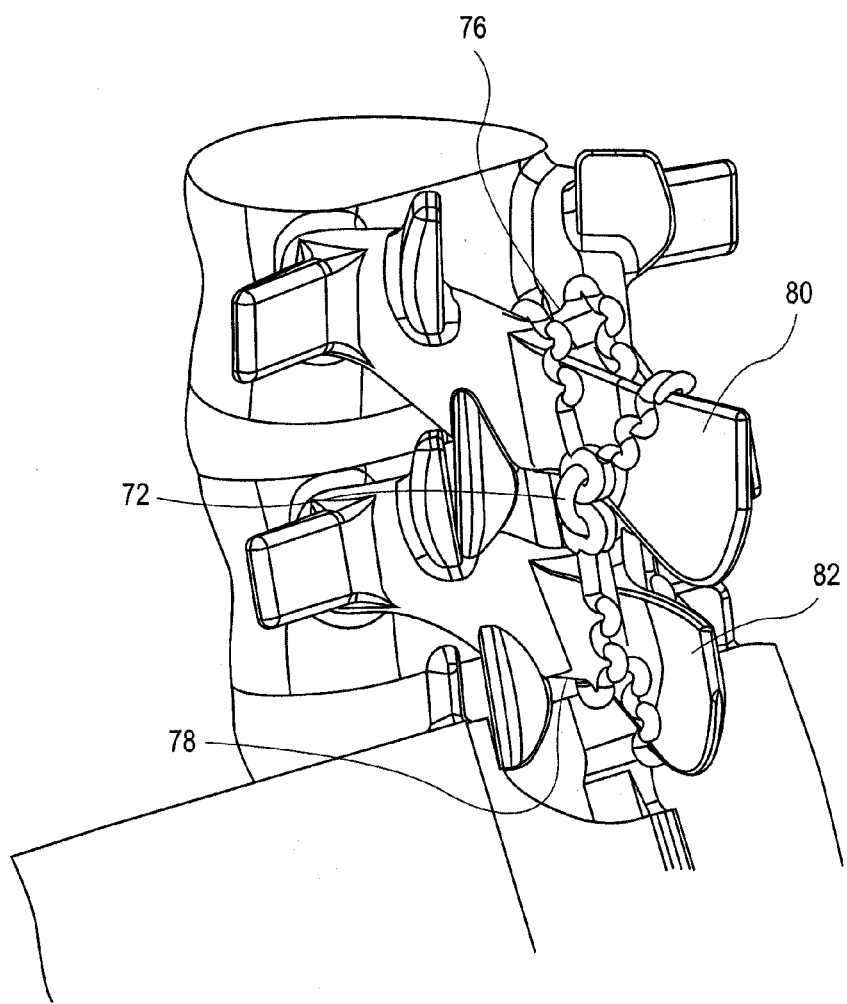
Figure 4C:
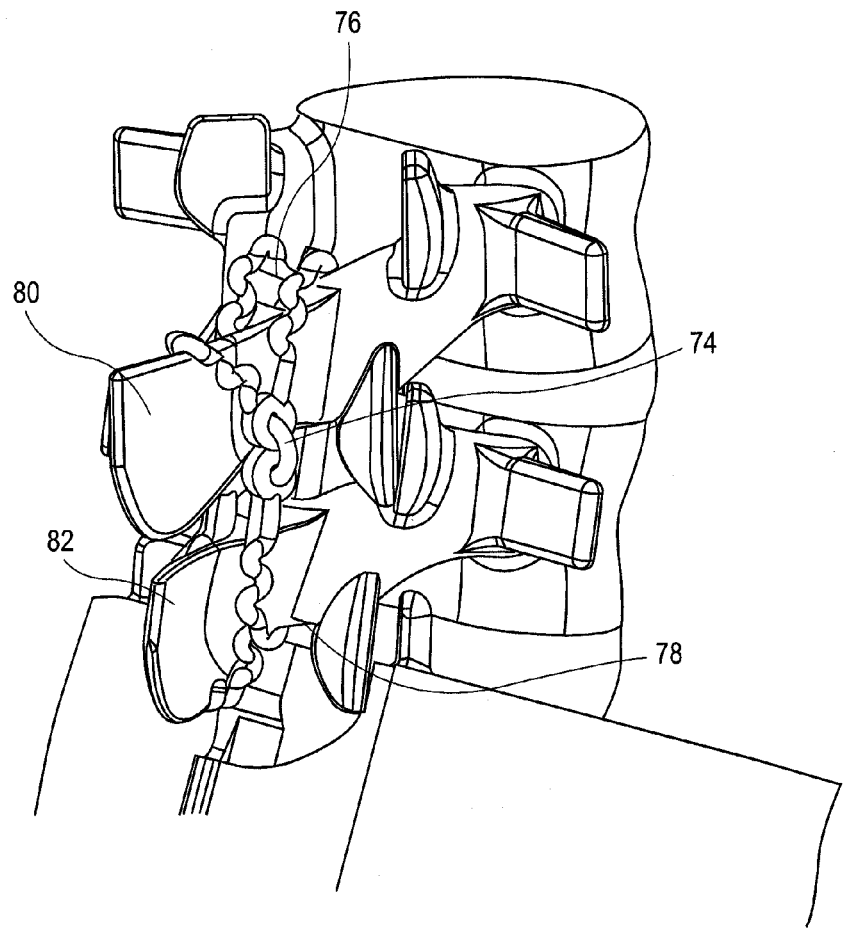

FIGS. 4a-4c show different views of an embodiment wherein the stabilization device comprises two of the stabilization devices shown in FIG. 2, but wherein each is on opposite sides of the midline "M". The stabilization device comprises two coupling elements 72 and 74, each of which is coupled to 4 different arms (as in FIG. 2), two of which are engaging lamina 76 and 78 of adjacent vertebrae, and two of which are engaging the spinous processes 80 and 82 of the two adjacent vertebrae. The coupling elements 72 and 74 are disposed substantially inferior to spinous process 80 and substantially superior to spinous process 82, and are disposed on opposite sides of midline "M".

Figure 5A:
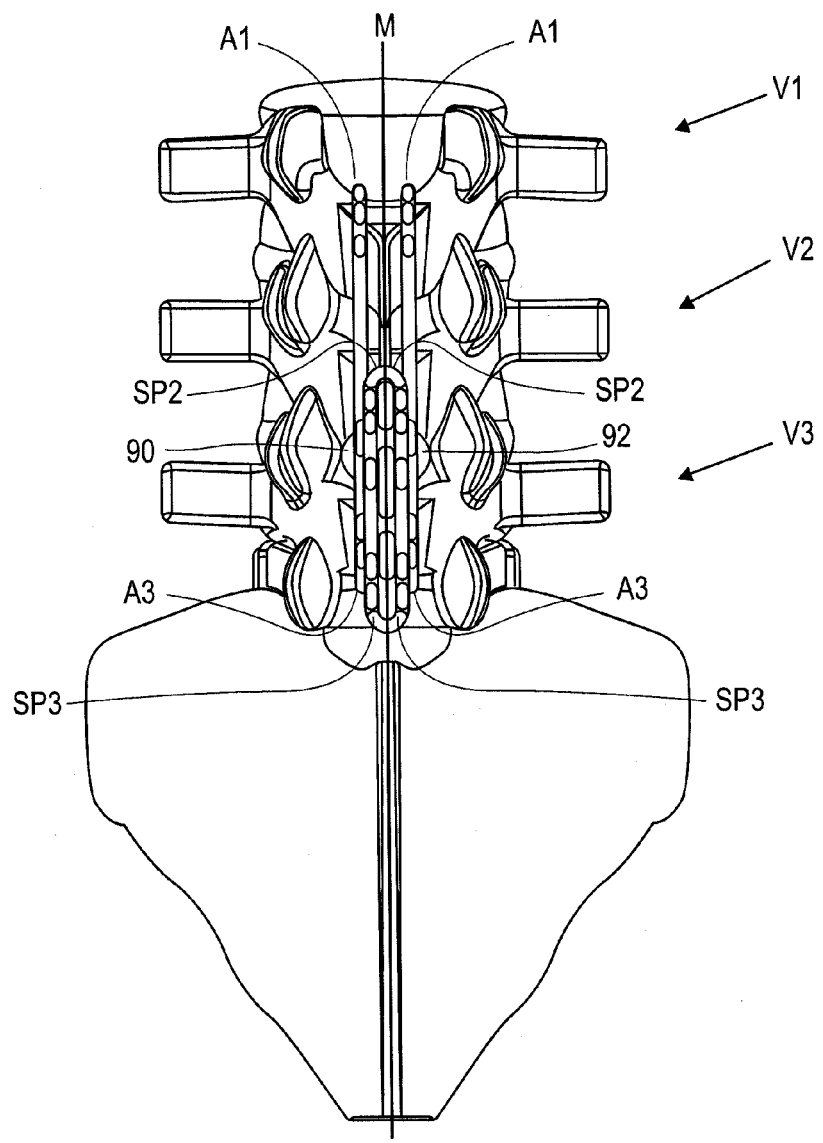
FIGS. 5a-5c show an embodiment of a spinal stabilization device engaging laminae and spinous processes of more than two vertebrae.
Figure 5B:
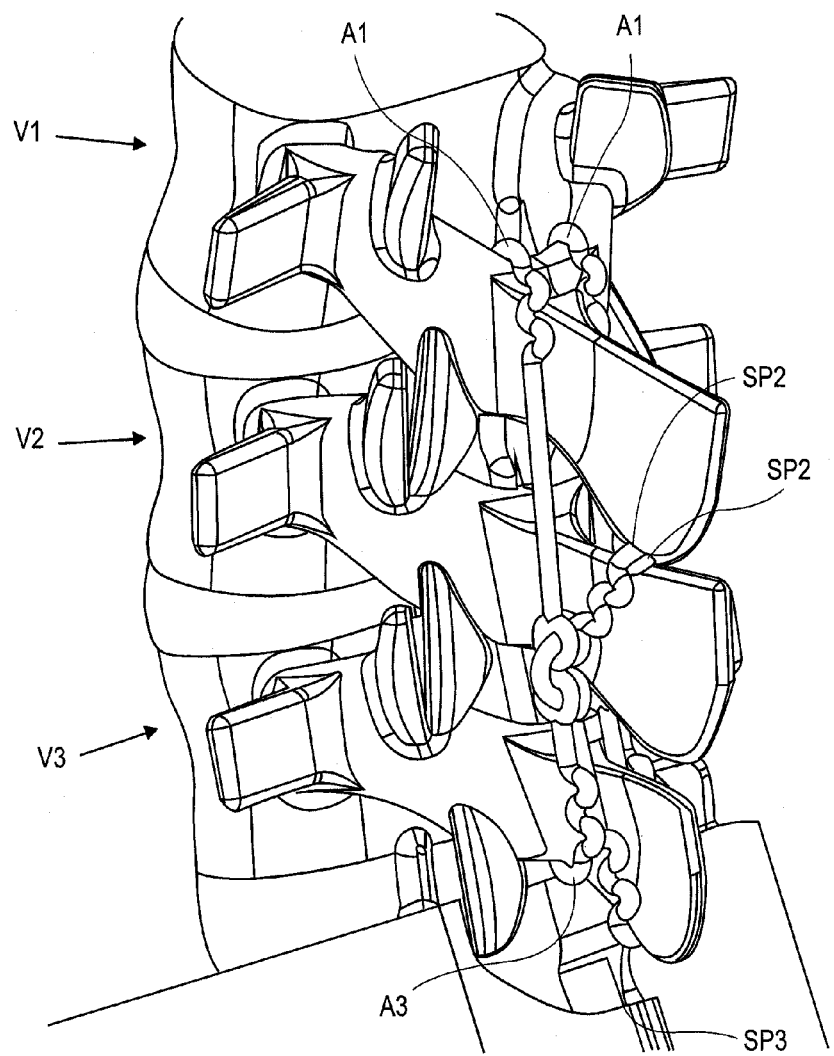
Figure 5C:
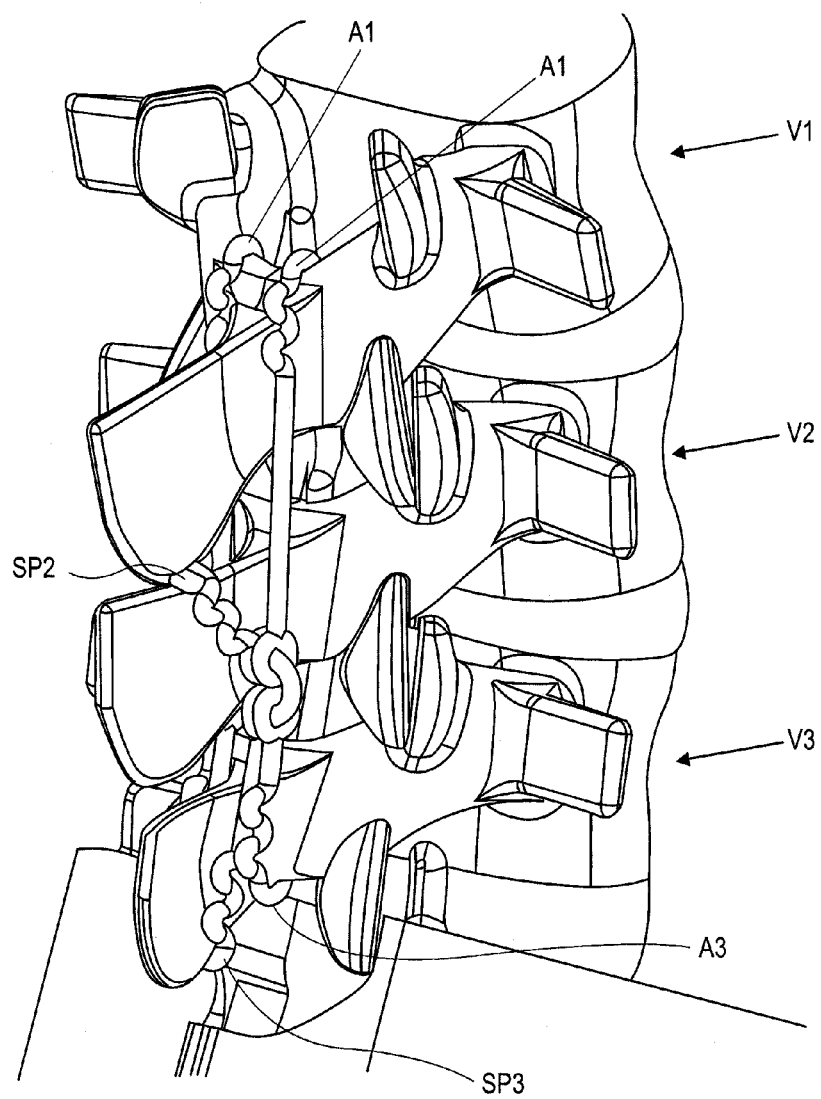

One advantage of the devices described herein is that by coupling a plurality of arms to a coupling element, each arm can be of a different length and can be adapted to engage a different vertebral structure. The arms can therefore engage both different vertebral structures (e.g., lamina, spinous process, etc.) as well as different vertebrae along the vertebral column. FIGS. 5a-5c show different views of an embodiment similar to the embodiment in FIGS. 4a-4c, with a Difference being that the arms engage more than two vertebrae. Arms A1 (which are coupled to two different coupling elements) are engaging the lamina of vertebra V1, while arms A3 are engaging the lamina of vertebra V3. Arms SP2 (which are coupled to different coupling elements) are engaging the spinous process of vertebra V2 and arms SP3 are engaging the spinous process of vertebra V3. The embodiment in FIGS. 5a-5c exemplifies how arms with a variety of lengths can be coupled to a coupling element and engage two or more vertebrae as well as different portions of the vertebrae.

The embodiments herein also illustrate how the engaging ends of the arms can be formed to be at different angles relative to the arm body to allow the engaging end of the arms to engage different vertebral structures. For example, in FIGS. 5a-5c, the engaging ends of arms SP2 formed such that they are rotated about 90 degrees with respect to the engaging ends of arms A1 and A3, which allows them to engage the spinous process. The engaging ends of arms SP2 are also shown to be set at about 90 degrees to the plane of the coupling end of the arms (the plane of the coupling ends of the arms is substantially parallel to the midline plane).

Figure 6A:
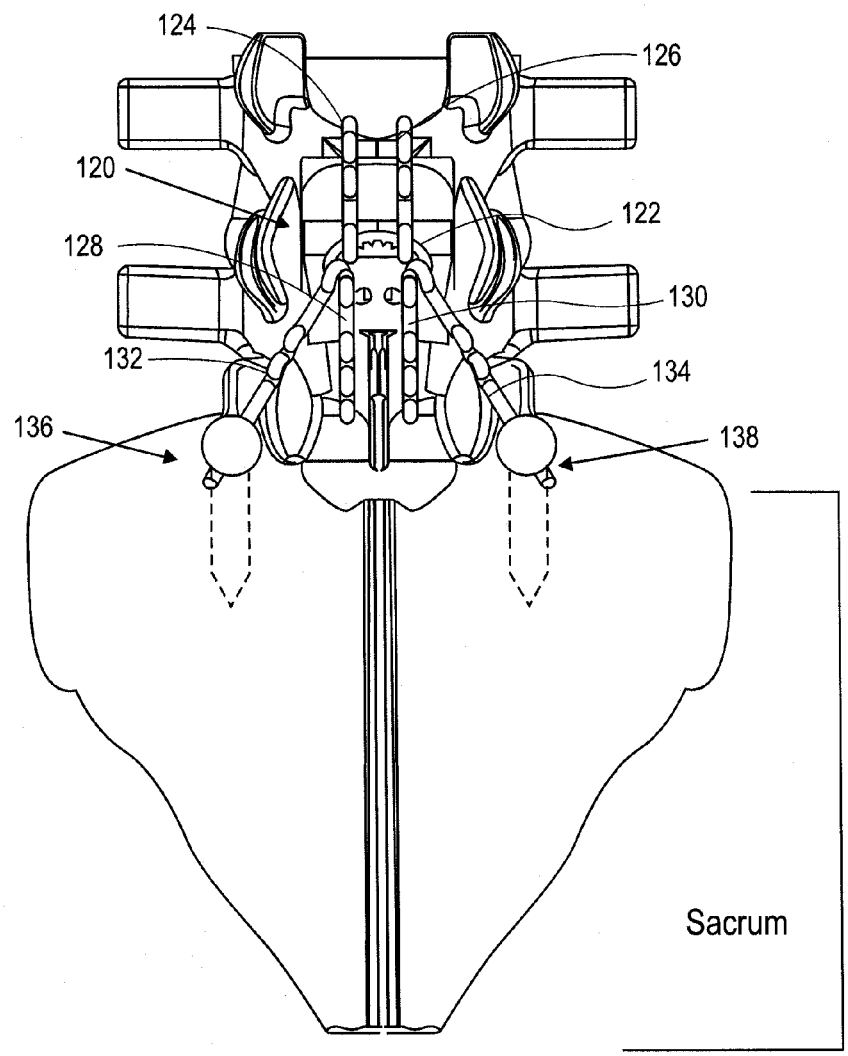
FIGS. 6a-6c show an embodiment of a spinal stabilization device including arms which are coupled to sacral anchors.
Figure 6B:
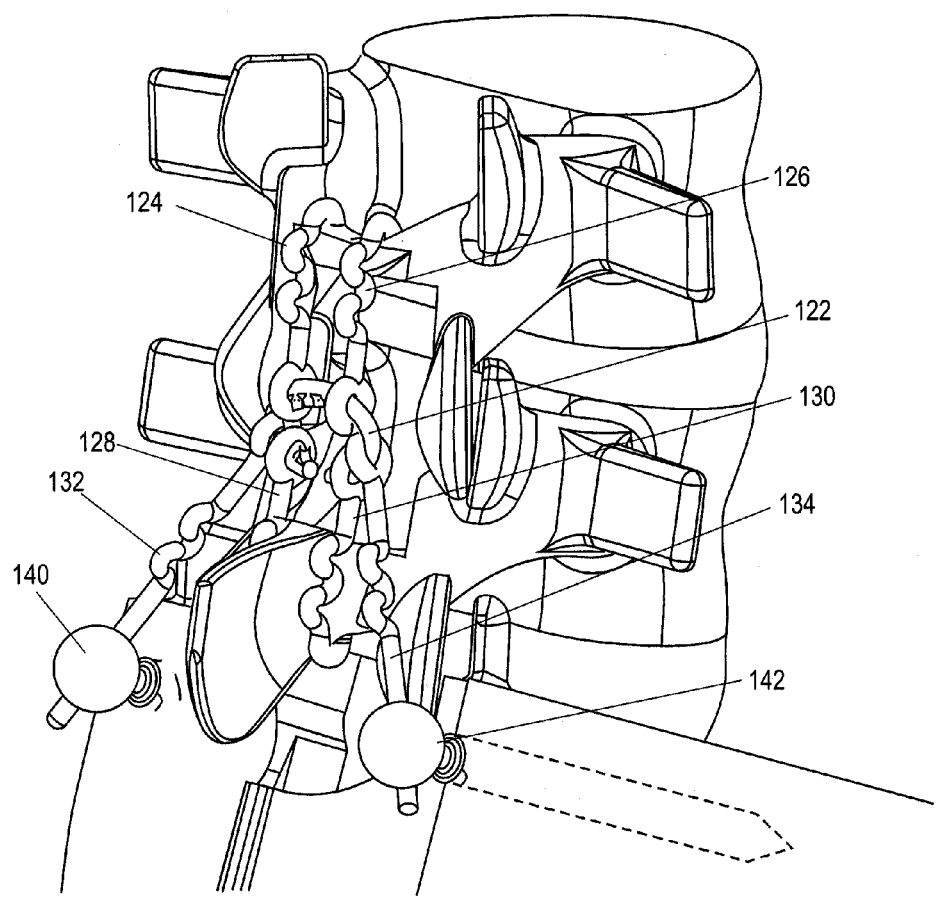
Figure 6C:
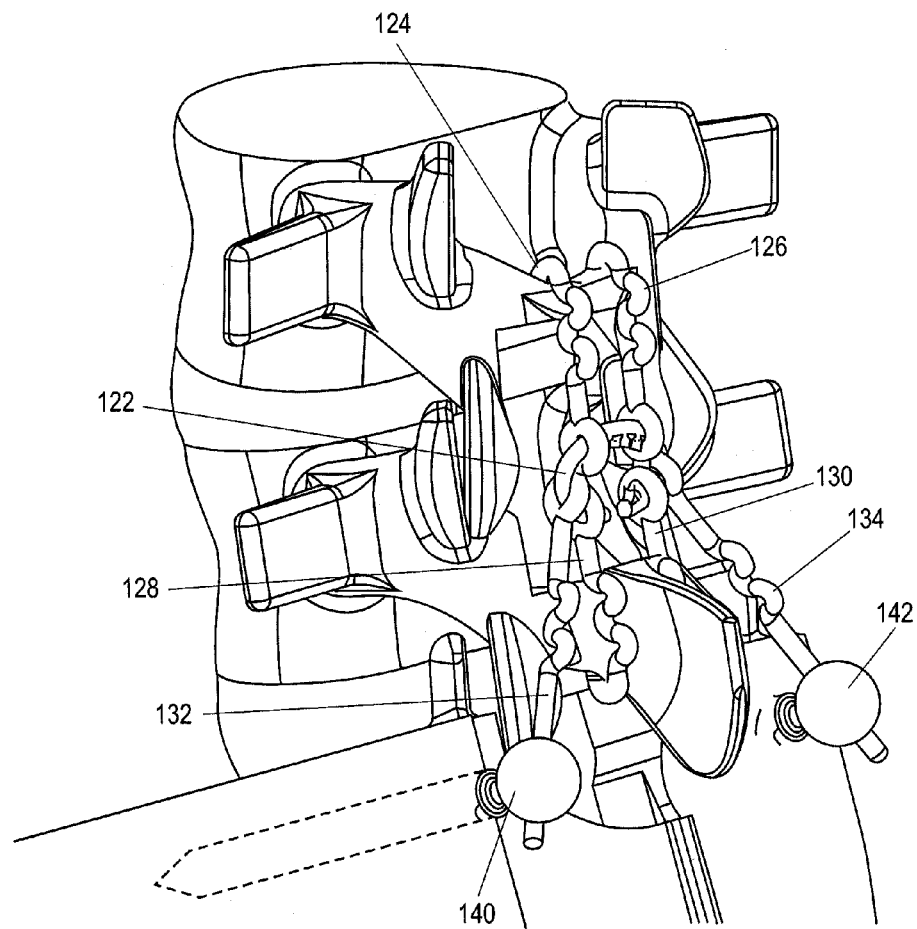

FIGS. 6a-6c show different views of an alternative stabilization device 120, which is similar to device 11 shown in FIGS. 3a-3c. Device 120, however, also comprises sacral anchors 136 and 138 coupled to arms 132 and 134. Arms 132 and 134 are also coupled to coupling element 122 as described herein. The sacral anchors can provide greater stability to the device and therefore also to the vertebrae.

Sacral anchors 136 and 138 can comprise threads to screw into the sacrum similarly to how pedicle screws are used to engage vertebrae. Widely available pedicle screws may in fact be used as sacral anchors 136 and 138. Arms 132 and 134 can be coupled to anchor heads 140 and 142 by a variety of mechanisms, but are shown passing through an internal bore in the anchor heads 140 and 142. The arms can be adhered within the bore with, e.g., an adhesive material.

The sacral anchors can, however, be screwed into areas of the vertebral column other than the sacrum. For example, the anchors can be pedicle screws which are screwed into one or more pedicles. The device can include any number of pedicle screws and the screws can be on either side of the midline.

The coupling elements described herein are generally engaged and coupled to the coupling ends of each of the plurality of arms of the stabilization device. Each of the arms has an end that engages the coupling element. The coupling elements shown herein have been shown with a generally annular, or ring-like, shape. The coupling ends of the arms have also been shown with a generally annular, or ring-like, shape, and are adapted to engage with the annular shape of the coupling element.

Figure 7:
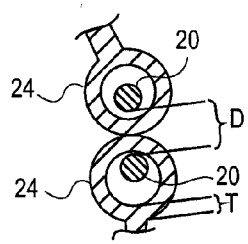
FIG. 7 shows a cross-sectional side view of an exemplary coupling element engaging two arm coupling ends.

FIG. 7 shows a cross-sectional side view of coupling element 20 from FIGS. 1-3, the coupling end 24 of arm 12, and the coupling end 24 of 14 (the other two arms not shown). The diameter of interior space "D" of coupling element 20 is at least twice the thickness "T" of coupling ends 24. This allows for at least two arms to be coupled inside the interior space D of the coupling element. In FIG. 7 the thickness "T" of the coupling ends is adapted such that the coupling ends of all four arms fit within the interior space of the coupling element. The thickness "T" of the coupling ends of the arms can be adjusted if needed to allow for additional arms to be coupled to the coupling element (e.g., by decreasing the thickness T of the coupling end) or the arm thickness can be increased to increase the rigidity or stability of the device. The thickness of the coupling ends 24 of one or more arms each coupled to the same coupling element can, however, be different. As described below, different stabilizing elements in the same coupling element can be sized and shaped differently to engage and constrain coupling ends with different sizes (e.g., thickness "T") or shapes.

Figure 8:
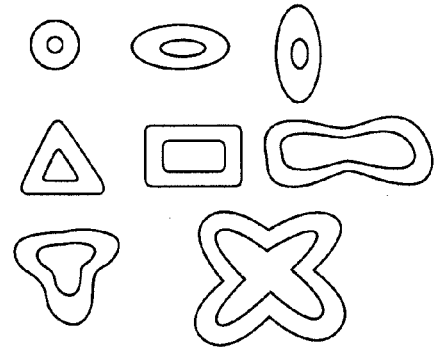
FIG. 8 shows exemplary cross-sectional posterior views of alternative coupling element shapes.
Figure 9:
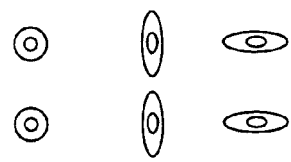
FIG. 9 shows cross-sectional side views of exemplary coupling elements.

The coupling elements shown in the figures above have a generally annular shape and circular cross-section (e.g., as can be seen in FIG. 7), however the coupling elements are not limited to such shapes and cross sections. FIG. 8 shows posterior cross-sectional views of exemplary alternative coupling element shapes. FIG. 9 shows side-views of cross sections of exemplary coupling elements.

Figure 10:
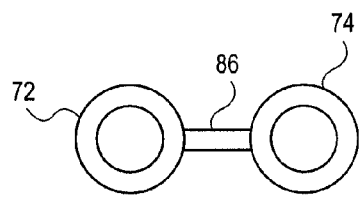
FIG. 10 shows a posterior view of an alternative coupling element.
Figure 11A:
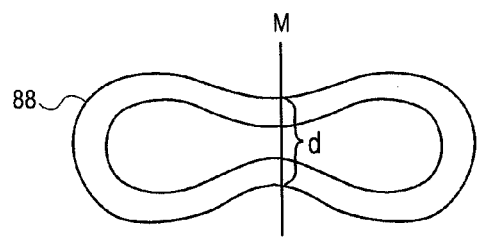
FIGS. 11a and 11b show alternative embodiments of coupling elements.
Figure 11B:
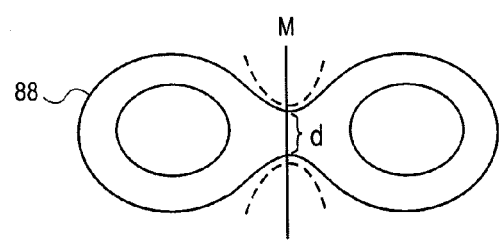

In the two embodiments shown in FIGS. 4a-4c and FIGS. 5a-5c, each stabilization device comprises two coupling elements. While the coupling elements are shown as discrete elements, they may be connected by connecting member 86 shown in FIG. 10. Connecting member 86 can stabilize the two coupling elements relative to one another and thereby create more stability between the vertebrae. Connecting member 86 in FIG. 10 is shown as a different element than coupling elements 72 and 74 (yet still attached to them). The coupling elements and the connecting member, can, however, be formed as an integral unit, such as coupling element 88 shown in FIGS. 11a and 11b. An integral unit such as coupling element 88 can stabilize the vertebrae even more than the coupling element shown in FIG. 10. Coupling element 88 shown in FIG. 11b has a smaller length "d" along midline M than length "d" shown in FIG. 11a. The coupling element in FIG. 11b also has two discrete spaces or openings to which the coupling ends of arms can be coupled. The embodiment shown in FIG. 11b can prevent arm coupling ends (not shown) from wandering over the midline while at the same time adding stability. The coupling elements 88 can be adapted to have a length "d" along the midline to create space for spinous processes (shown in phantom in FIG. 11b), which need not be removed prior to implantation of the stabilization device. The external surface of coupling elements 88 can even be adapted to engage the spinous processes for added stability.

Figure 12A:
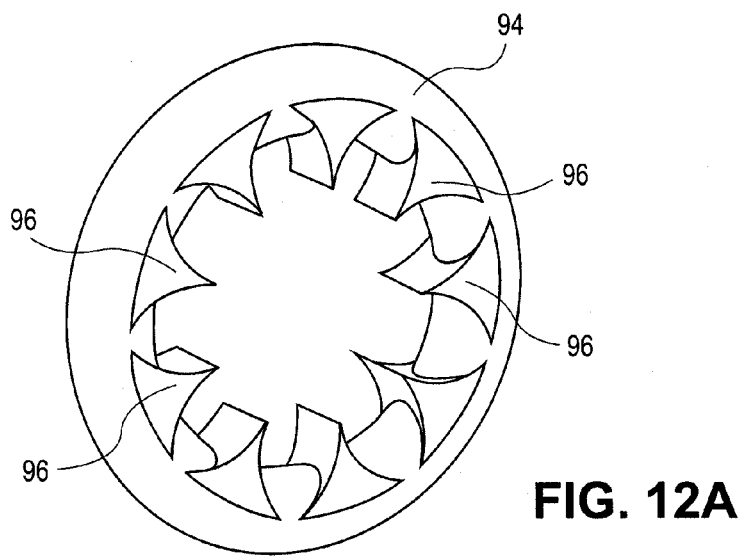
FIGS. 12a and 12b show alternative embodiments of coupling elements including arm stabilization elements.
Figure 12B:
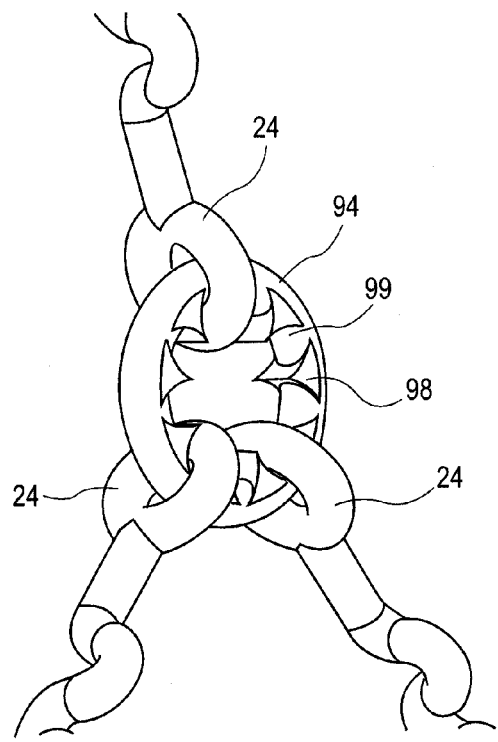

FIGS. 12a and 12b illustrate an exemplary embodiment of coupling element 94 comprising arm stabilization elements 96. There are nine (9) stabilization elements shown but this is not intended to be limitation, as more or fewer may be incorporated into the coupling element (in fact there may be none). Arm stabilization elements 96 are generally configured to constrain the coupling ends of the arms to a limited space within coupling element 94. The arm stabilization elements need not physically engage coupling ends of the arms, but rather can be adapted to simply prevent unwanted movement of the coupling ends within the coupling element. The stabilization elements and the coupling ends, however, may be adapted to snugly engage one another to substantially prevent movement between the two. Arm stabilization elements 96 are shown generally shaped to engage and mate with the shape of coupling ends 24. Arm stabilization elements 96 as shown comprise peaks 98 and valleys 99 in the interior of coupling element 94. In some embodiments valleys 99 are simply the inner surface of coupling element 94. The stabilization elements define spaces which are adapted to receive the coupling ends 24 of the arms. The peaks and valleys are adapted to mate with the coupling ends of the arms. As shown, each arm coupling end is constrained by two arm stabilization elements. The coupling ends may or may not actually engage the stabilization element. The stabilization elements can simply have complimentary shapes to the arm coupling ends and can help constrain the coupling ends within the coupling element. Each stabilization element, need not, however constrain an arm coupling end. For example, nine (9) stabilization elements are shown, but only six (6) of them are constraining a coupling end 24. Any of the coupling elements describe herein may comprise one or more arm stabilization elements.

Figure 13A:
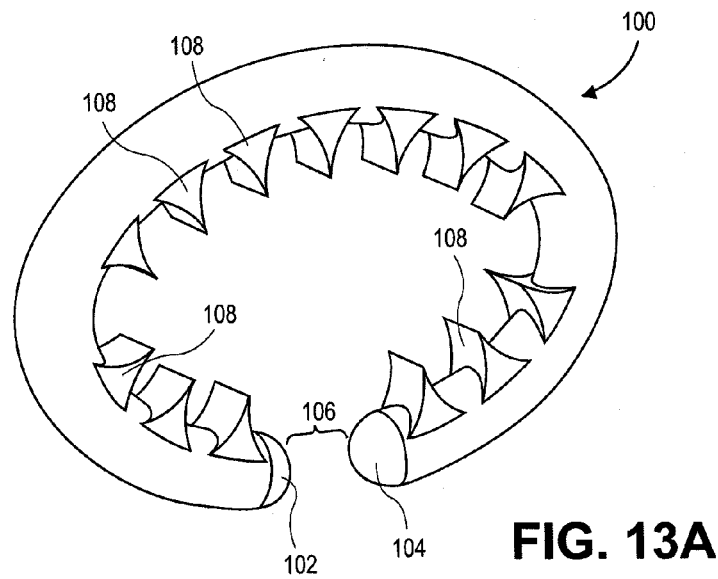
FIGS. 13a-13c show alternative coupling elements including a discontinuity or space defined by its two ends.
Figure 13B:
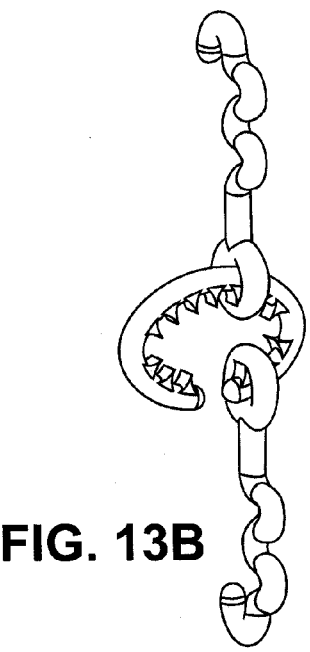
Figure 13C:

FIGS. 13*a*-13*c* illustrate an alternative embodiment of coupling element 100 comprising first end 102 and second end 104, the two ends creating discontinuity or space 106. Also shown are arm stabilization elements 108. Discontinuity 106 can allow the coupling ends of the arms to be positioned into or removed from coupling element 100. Coupling element 100 can be disposed in the patient such that the discontinuity is opening (i.e., facing) in any direction. FIGS. 13*b* and 13*c* show two exemplary orientations of the coupling element. Any of the coupling elements described herein can include a discontinuity or space.

FIG. 14 is a posterior view of an alternative embodiment of coupling element 110 comprising coupling element divider 112 which is adapted to separate or divide the arms (not shown) which engage a superior vertebra and the arms (not shown) which engage an inferior vertebra. The dividers 112 (the coupling element may alternatively only comprise one divider) can increase the stability of the arms within the coupling element, which can increase the stability of the device. The divider can also comprise arm stabilization elements (not shown) that have been described herein that are shaped to mate with the engaging end of the engaging ends of the arms.

FIG. 15 shows the ends of an alternative coupling element with an optional lock. The lock comprises male element 122 on one end of the coupling element and female element 124 (shown in phantom) disposed within the other end of the coupling element. By advancing male element 122 into receiving female element 124 (which may occur from physician actuation of the coupling element or when the coupling element reverts to a memory configuration, as is described below), the two ends of the coupling element can be reversibly locked together. The lock can be almost any mechanism to allow one end of the coupling element to securely engage the other end of the coupling element. The lock may be reversibly or irreversible. Any of the coupling elements described herein can incorporate a lock element such as the lock shown in FIG. 15.

The lock can be adapted to be releasable, or reversible, if at any point during the implantation procedure (or after the procedure, such as during a subsequent surgical procedure) the lock must be unlocked to, for example, reposition an arm into a different arm stabilization device, to substitute an arm with an arm of a different length, to replace an arm that is engaging one vertebral structure with an arm that is adapted to engage a different vertebral structure, or to remove the entire device from the patient. FIG. 15 shows lock release elements 126 which when actuated in the direction of the arrows shown, will collapse elements 128, allowing the male element 122 to be removed from female element 124, thereby unlocking the lock.

FIGS. 16 and 17 show an alternative coupling element that operate similar to a carabiner, with a door 300 comprising a spring hinge 302. The coupling ends of the arms (not shown) can be pushed against the door causing the door to open (the configuration shown in FIG. 16), allowing the arm coupling end to be positioned within the interior of the coupling element. Once pressure is no longer applied to the door element, the spring hinge causes the door to close (shown in FIG. 17), securing the arm within the coupling element. If at any time during the procedure or at a follow up date, the physician can open the door to remove, or adjust the position of, any of the arms. The door can then again be closed. Such a door allows for adjustment or removal of any of the arms at any point during or after the procedure. Any of the coupling elements described herein may comprise the features described with respect to FIGS. 16 and 17.

Figure 18:
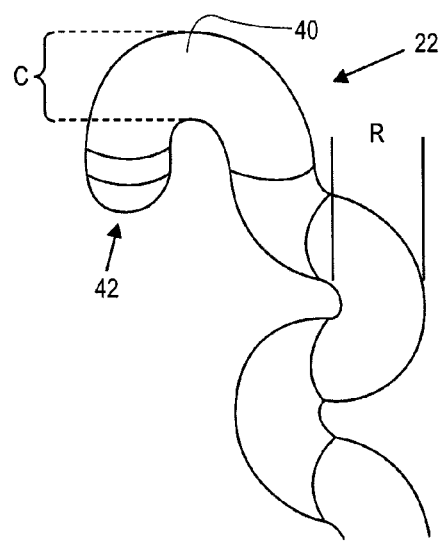
FIGS. 18-20 show alternative arm engaging ends.
Figure 19:
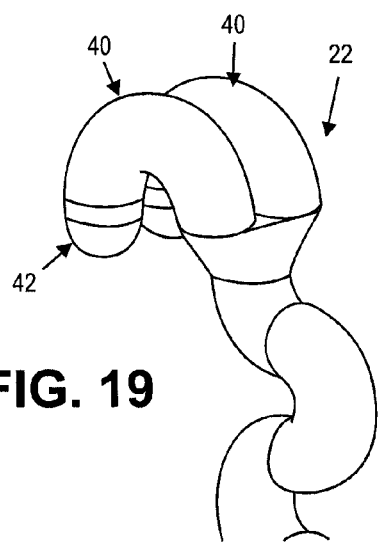
Figure 20:
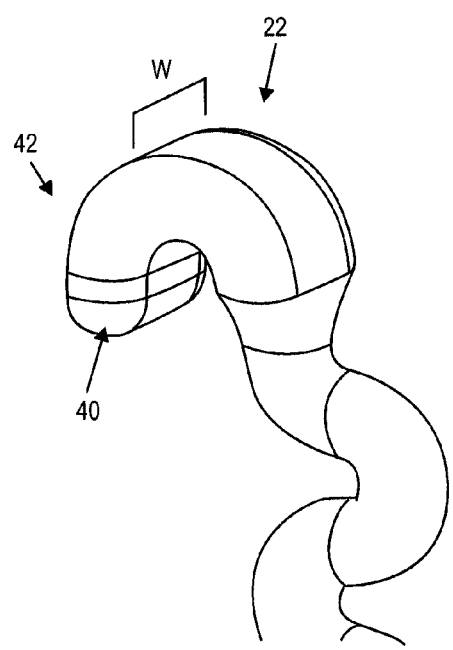

FIG. 18 shows an exemplary engaging end 22 of one of the arms shown in FIGS. 1, 2, and 3. Engaging end 22 has a generally semi-circular configuration and is adapted to hook onto a lamina, thereby acting as a hook element. The thickness "C" of engaging end 22 is shown substantially the same as thickness "R" of the arm body. FIG. 19 shows an alternative engaging end 22 comprising a plurality of engaging members 40 adapted to engage a vertebra section, whereas FIG. 18 shows a single engaging member 40. FIG. 20 shows engaging end 22 comprising a single engaging element 40 with width "W" which is generally twice the width "C" of the engaging members shown in FIGS. 18 and 19. That is, width "W" is about twice the thickness "R" of the arm body. Engaging ends comprising multiple engaging elements or engaging elements of increased width can be used to more evenly distribute the force applied by the engaging end over a larger segment of the bony structure to more securely engage the bone and also to provide added stability to the vertebrae.

The engaging ends described herein which are adapted to engage a lamina are generally adapted to minimize the area of the engaging end that enters the vertebral foramen, thus minimizing the disruption to the spinal cord. Only the distal end 42 of the engaging end as shown herein is adapted to hook over a lamina and enter the vertebral foramen. The engaging ends in the form of a hook can also, however, be adapted to engage vertebral structures other than a lamina (e.g., a spinous process).

FIG. 1 shows the longitudinal axis of arm 12 disposed at angle "R" relative to the longitudinal axis of arm 16 (as viewed from the side). The arms can be disposed at almost any angle to each other based on the rotational engagement that can occur between the coupling element and the coupling ends of the arms (i.e., the coupling ends and the coupling element are shaped such that the annular coupling end can be rotated around a portion of the coupling element). One of the advantages of the devices described herein is therefore that different arms can engage different vertebral structures (such as, e.g., the lamina and the spinous process as shown). The ability of the arms to apply stabilizing forces in different directions to different vertebral structures (as opposed to being able to engage only the laminae or only the spinous process and apply forces only in one plane or in one direction) also enhances the stabilization abilities of the device.

As each of the arm engaging ends can be adapted to be able to engage a different vertebral structure (e.g., lamina, spinous process, transverse process), the plane in which the engaging end of the arm is disposed can be at an angle to the plane in which the arm body is generally disposed. In FIGS. 1 and 2, the plane in which the engaging ends of arms 16 and 18 are disposed are at roughly a 90 degree angle to the plane in which the arm body is generally disposed (the plane in which the arm body is generally disposed is substantially parallel to the midline plane). This angle allows the engaging arms to engage the two spinous processes as shown in FIG. 2. The engaging end may however be adapted to assume an additional different orientation relative to the general longitudinal axis of the arm body. FIG. 21a shows a side-view of an alternative embodiment of engaging element 22 at a different orientation from the arm body 44. The engaging end 22 is oriented at angle "A" from the longitudinal axis "LA" of arm body 44. FIG. 21b shows a posterior view of the arm in FIG. 21a, including the coupling to coupling element 20. FIG. 21b additionally shows engaging end 22 engaged with spinous process 34. The engaging arm 22 can be oriented at angle A or any other angle to, for example, more securely, and/or more naturally, engage the spinous process.

While FIGS. 1-3 show the stabilizing device comprising four (4) arms, the device can have more or fewer arms. The device can comprise 2, 3, 4, 5, 6, 7, 8, 9, 10, or more arms. The device can have an even or odd number of arms. The arms can be disposed either on the same side of the midline or on different sides of the midline.

In addition, the engaging end of at least one arm could be coupled to a second coupling element disposed at upper or lower spine locations, which could have additional arms coupled thereto. The number of arms and coupling elements shown and described herein is therefore not intended to be a limitation of the invention.

The arms can be adapted such that they can be anchored to a variety of vertebral structures. In preferred embodiments the arms are adapted to hook, or grab, onto a vertebral structure. One exemplary location is the lamina, as is shown in several embodiments herein. Any or all of the arms can, however, be adapted to engage other vertebral structures to provide stabilization (spinous process, transverse process, facets, etc).

At least one arm of the stabilization device includes a length adjustment element, which has a first configuration prior to stabilization and a second configuration which increases the stabilization between at least two vertebrae. The length adjustment element can be a discrete element disposed between the engaging end and the coupling end, or the length adjustment element can also be shape memory characteristics of the arm material.

Figures 24A, 24B:
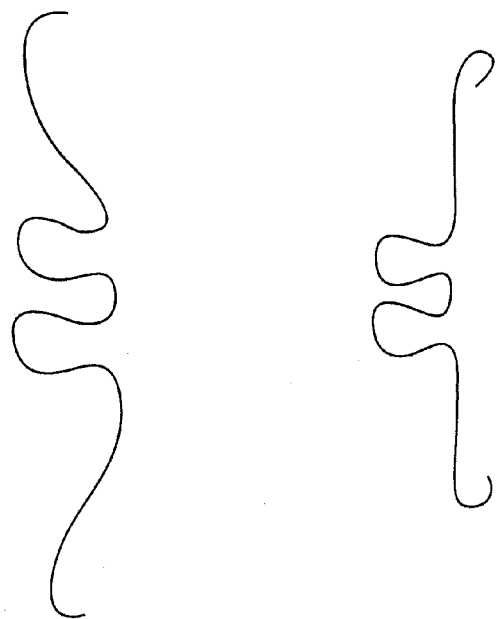
FIGS. 24a and 24b show a prior art device in deformed and memory configurations, respectively.

The Davydov shape memory loop from CJSC KIMPF Company, Moscow, Russia (part of the KIMPF-DI Fixing shape memory implant system) is made of Nitinol and can be deformed to a temporary configuration when cooled below a particular temperature, and will assume a memory configuration when heated above a particular temperature. FIGS. 24a and 24b show the Davydov shape memory loop in a deformed and memory configuration, respectively.

Figure 25B:
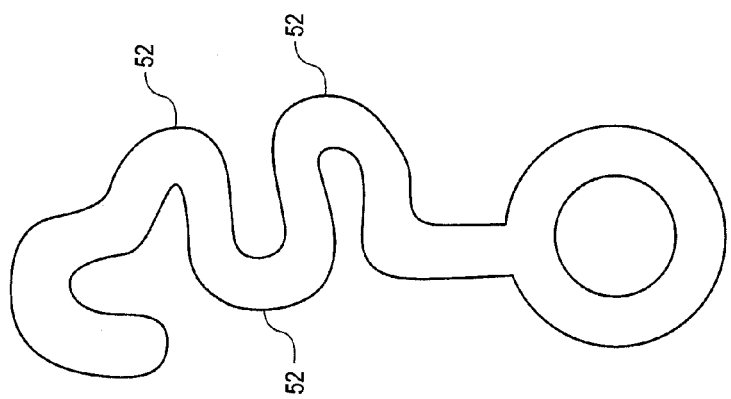
FIGS. 25a and 25b show an exemplary arm in a deformed configuration and a memory configuration, respectively.
Figure 25A:
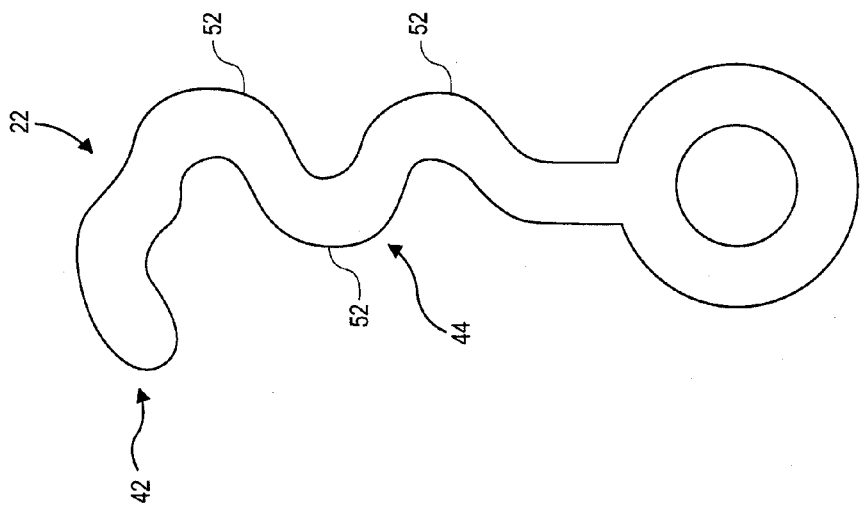

The arms of the stabilization devices described herein can also be configured to be heat set, similar to the Davydov loops. They can be made from a shape memory material such as Nitinol. FIGS. 25a and 25b show an exemplary arm in a first deformed configuration and a second memory configuration, respectively. Any of the arms described herein can be made of shape memory material and can be heat-set so that they are adapted to be deformed into a first configuration and can assume a memory configuration to stabilize at least two vertebrae.

Figure 22:
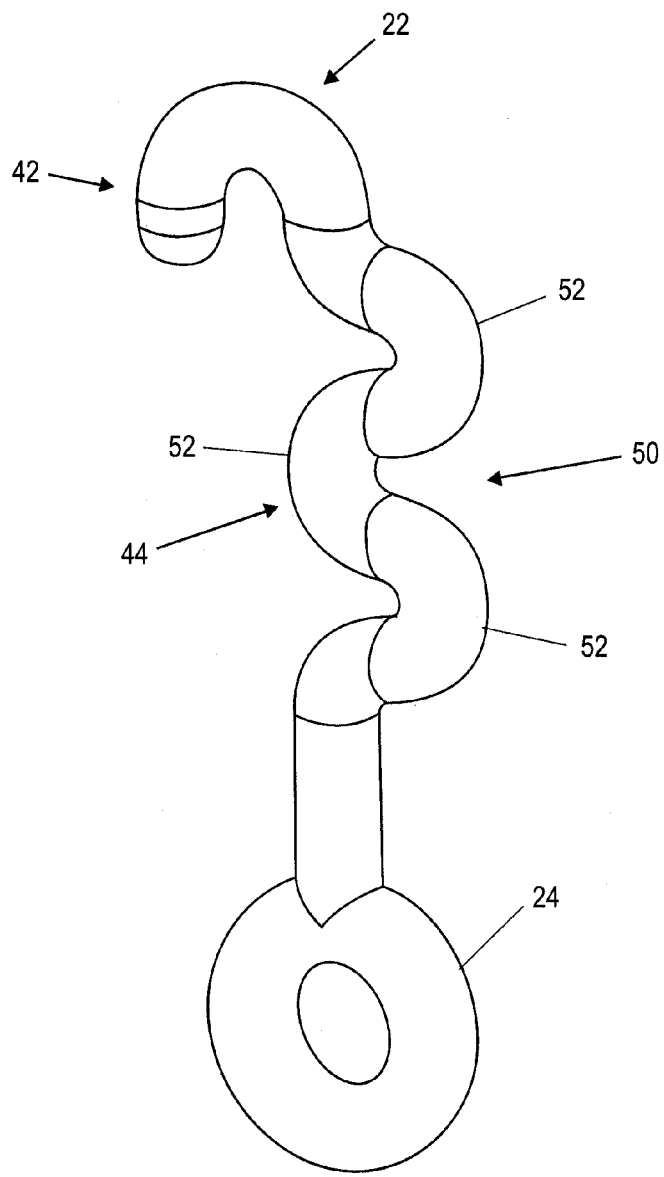
FIG. 22 shows an exemplary arm.

The arm bodies can be formed with almost any number of different shapes and/or configurations. FIG. 22 shows arm 50 with arm body 44 and flexibility elements 52 in the form of turns in the arm body. The flexibility elements can provide a degree of flexibility to the arms (and to the device overall) such that the device provides stabilization to the spine while allowing for a small degree of flexibility in response to natural movement between vertebrae.

Elements 52 can also be the length adjustment elements as shown in FIGS. 25a and 25b. Elements 52 in FIGS. 25a and 25b are heat-set as described above. As shown in FIGS. 25a and 25b, elements 52 comprise bends in the arm body and are tighter in the memory configuration in FIG. 25b. That is, the bends have smaller radii of curvature in the memory configuration. This decreases the length of the arm body and therefore decreases the distance between the engaging end and the coupling end of the arm. This decrease in distance increases the stabilization between vertebrae.

Figure 23:
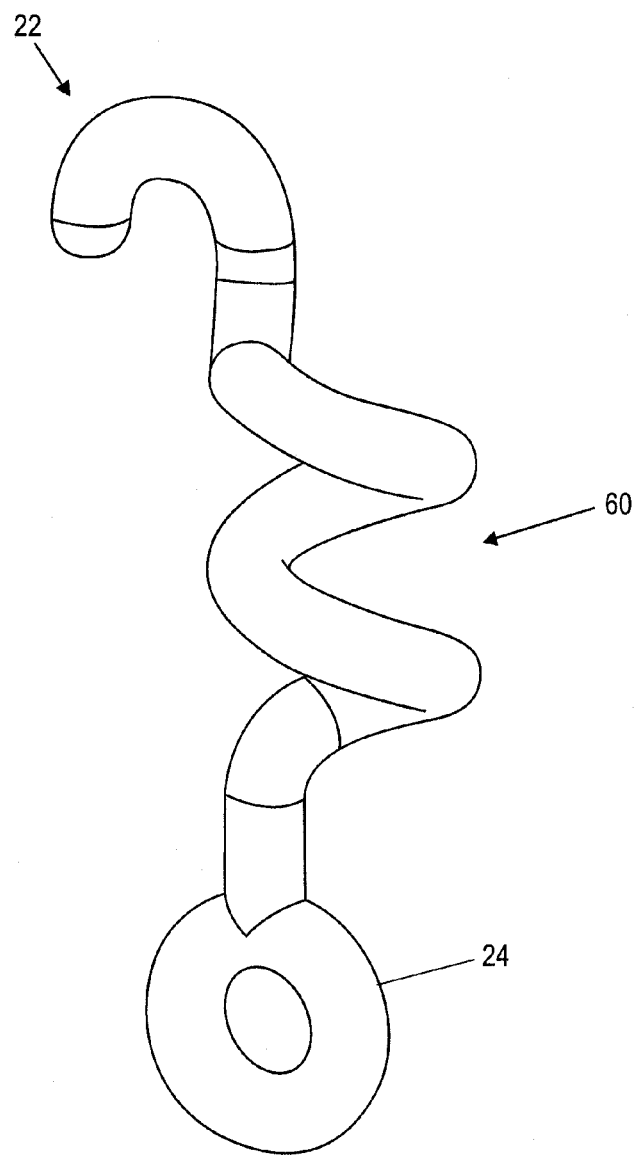
FIG. 23 shows an exemplary arm comprising a coil element.

FIG. 23 shows an alternative embodiment of an arm wherein the flexibility element (or length adjustment element) comprises spring element 60. The length adjustment element can be spring 60 such that the spring is heat-set to assume a tighter coil in the memory configuration (not shown). The constriction of the coil shortens the distance between the engaging end and the coupling end, thereby increasing the stabilizing forces to the vertebrae.

As shown in FIGS. 25a and 25b, the engaging end 42 can also be heat set such that is assumes an open configuration to enable the physician to position the engaging end around the lamina. When the device is heated above its transition temperature as explained below, the engaging end will assume a more constricted configuration as shown in FIG. 25b, which will secure the engaging end to the lamina (or other vertebra structure).

The entire arm or only a portion of the arm can be made of shape memory material such as Nitinol. In one merely exemplary embodiment the arms have a temperature characteristic such they are in a martensite phase at a temperature of 10° C. and below and in an austenite phase at a temperature of more than 35° C. to return back to a memory original shape. The deformed shape is kept unchanged up to 26° C. and the memorized shape is gradually restored by a heat treatment up to 35° C. The arms are set in the memory configuration by performing a heat treatment at a temperature of about 650° C. to about 750° C. for about one hour. When ready for implantation, the arms are exposed to saline at a temperature of 10° C. or below and the arm is deformed to its deformed, or first, configuration. This deformed configuration will allow the arm to be easily positioned within the coupling element.

All or fewer of the following method steps may be included in the method of implantation. Additionally, the order of the method is not limited to the order recited herein, as the order of the steps may be adjusted to perform the implantation. One exemplary method of implantation after deformation of the arms is now described in reference to FIGS. 3a-3c. The coupling end of arms 13, 15, 17, and 19 are engaged with coupling element 21. This is done by advancing the coupling ends through the discontinuity in coupling element 21. The engaging ends of arms 13, 15, 17, and 19 are then positioned adjacent the lamina of vertebra L4 and L5. A heat treatment is applied to the arms at a temperature of more than 35° C. using a heating source such as saline. This causes the length adjustment element in the arms (or in fewer than all the arms if not all arms include a length adjustment element) to assume their memory configuration. The engaging ends of each of the arms may hook on the vertebral structures more securely in the memory configuration as described above. This generally shorter memory configuration causes force to be applied to the lamina generally parallel to the axis of the spine. These compressive forces increase the stabilization of the vertebrae.

Alternatively, only arms 13 and 17 may initially be positioned with the coupling element. The engaging ends of arms 13 and 17 can then be positioned adjacent lamina 26. While holding the coupling element (engaged to arms 13 and 17) with a first surgical tool, the physician can then use a second surgical tool to position the coupling end of arm 15 into the interior space of coupling element 21 and to position the engaging end of arm 15 with lamina 28. Arm 19 can then be positioned in the same manner using the second surgical tool.

Figure 26A:
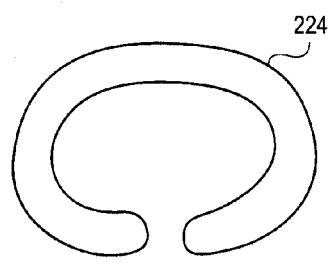
FIGS. 26a and 26b show an exemplary coupling element in a deformed configuration and a memory configuration, respectively.
Figure 26B:
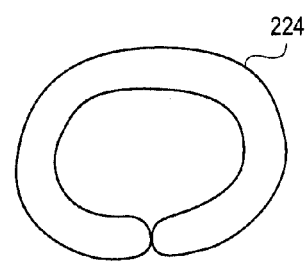

In an alternative embodiment, the coupling element can also be heat set with a first deformed configuration and a second memory configuration. FIGS. 26a and 26b show an exemplary coupling element 224 in a deformed, open, configuration, and a memory, closed, configuration, respectively. Coupling element 224 can be cool and heated in the same manner as the arms described above. Coupling element 224 can be deformed into the open configuration shown in FIG. 26a to allow a physician to position the coupling ends of arms within coupling element 224. The physician can then heat treat coupling element 224 so that it assumes its closed memory configuration shown in FIG. 26b. In the closed configuration in FIG. 26b, the ends of the coupling element are disposed close to one another, if not actually touching. The distance between the ends of the coupling element in the closed configuration may be set such that the distance is less than the thickness of the coupling ends of the arms. This will prevent the arm coupling ends from being released from the coupling element. If the device needs to be adjusted at any time after the procedure as described above, the coupling element may be cooled into its martensite phase and deformed to its open configuration shown in FIG. 26a. The arms may then be adjusted as described above, or the entire device may be removed from the patient.

A coupling element that is heat treated can be used with any of the stabilization devices described herein. In some embodiments the device includes a coupling element and a plurality of arms, all of which have first and second configurations. When the device is heat treated, the coupling element and the arms will assume their memory configurations. The change of the coupling element to the closed memory configuration secures the arms within the coupling element as well as increases the stabilization between vertebrae.

Referring back to FIG. 22, the number of flexibility elements 52 (or length adjustment elements) is not limited to that described above. FIG. 22 shows three (3) flexibility elements along the length of arm body 44, but the arm could be adapted to have more or less, such as 1, 2, 4, 5, or more. Also included in the invention are kits that include a plurality of arms with different lengths and/or different numbers of flexibility elements. In use, the physician can measure the distance between vertebral structures that are to be engaged, and then choose arms from the kit based on their length and or the number of flexibility elements/length adjustment elements to ensure the device spans the correct length and achieves the desired amount of stabilization.

In some embodiments, the arms may simply have straight configuration without any flexibility elements or they may not comprise any shape memory materials.

The stabilization devices described herein can be used alone or in combination with other stabilization devices (e.g., pedicle screws, the X STOP®) or other stabilization procedures. For example, the devices can be used to stabilize vertebrae after fusion procedures are performed, perhaps making it unnecessary to use pedicle screws.

What is claimed is:

1. A vertebral stabilization system comprising:
    a first arm comprising
        a first engaging end adapted to directly engage a first vertebral structure of a first vertebra,
        a first coupling end, and
        a length adjustment element comprising a plurality of bends aligned in the same plane, the plurality of bends being adapted to change configuration in response to thermal activation to cause the length adjustment element to shorten, the first engaging end and the first length adjustment element a monolithic structure;
    a second arm comprising
        a second engaging end adapted to directly engage a second vertebral structure of a second vertebra and
        a second coupling end; and
    a coupling element directly engaged with the first coupling end and the second coupling end, wherein the coupling element comprises a plurality of arm stabilization elements disposed around an inner portion of the coupling element, each of the plurality of arm stabilization elements configured to stabilize the first coupling end and the second coupling end in one of a plurality of different positions with respect to the coupling element.

2. The system of claim 1 wherein the second arm further comprises a second length adjustment element, the second length adjustment element having a first configuration with a first length and a second configuration with a second length, wherein the second length of the second length adjustment element is different than the first length of the second length adjustment element.

3. The system of claim 1 wherein the first engaging end comprises a hook element adapted to hook onto the first vertebral structure.

4. The system of claim 1 wherein the first length adjustment element is made of an elastic material.

5. The system of claim 4 wherein the elastic material is a shape memory material.

6. The system of claim 4 wherein a plurality of bends each have a first radius of curvature in a first configuration and a second radius of curvature in a second configuration, wherein the second radius of curvature is less than the first radius of curvature.

7. The system of claim 1 wherein the first coupling end has an annular configuration.

8. The system of claim 7 wherein the coupling element has a substantially annular configuration, and wherein the first coupling end and the coupling element directly engage one another in a chain-like manner.

9. The system of claim 1 further comprising a third arm comprising
    a third engaging end which is adapted to directly engage a third vertebral structure of the first vertebra, wherein the first vertebral structure and the third vertebral structure are different structures, and a third coupling end directly engaged with the coupling element.

10. The system of claim 1 wherein the coupling element has a substantially annular configuration with a first end and a second end, wherein the first end and the second end define a discontinuity in the substantially annular configuration.

11. The system of claim 1 further comprising a third arm with a third engaging end and a third coupling end, and a fourth arm with a fourth engaging end and a fourth coupling end, wherein the third coupling end and the fourth coupling end are directly engaged with the coupling element, and
wherein the first and second arms are adapted to directly engage the coupling element such that they are disposed on one side of the midline of the spine, and wherein the third and fourth arms are adapted to directly engage the coupling element such that they are disposed on the other side of the midline of the spine.

12. The system of claim 11 wherein the first engaging end, the second engaging end, the third engaging end, and the fourth engaging end each comprise a hook element adapted to hook onto a lamina.

13. The system of claim 1 further comprising a third arm with a coupling end directly engaging the coupling element and a second end fixedly coupled to a sacral anchor.

14. The system of claim 1 wherein the first length adjustment element has a coil configuration.

15. The system of claim 1 wherein each of the plurality of arm stabilization elements are configured to stabilize the first coupling end and the second coupling end in one of a plurality of different orientations with respect to the coupling element.

16. The system of claim 1 wherein the coupling element has an annular configuration and the plurality of arm stabilization elements are disposed around an inner portion of the annular configuration.

17. The system of claim 16 wherein the first and second coupling ends have ring configurations.

18. The system of claim 1 wherein the plurality of arm stabilization elements is at least three arm stabilization elements.

19. The system of claim 1 wherein the coupling element has an annular configuration with a central opening, and the first and second coupling ends each comprise a ring.

20. A spinal stabilization system, comprising:
a first elongate member comprising
a first engaging end with a first hook element adapted to directly engage a lamina of a first vertebra,
a first coupling end, and
a length adjustment element disposed between the first engaging end and the first coupling end, the length adjustment element comprising a plurality of bends aligned in the same plane, the plurality of bends being adapted to change configuration in response to thermal activation to cause the length adjustment element to shorten;
a second elongate member comprising
a second engaging end with a second hook element adapted to directly engage a lamina of a second vertebra and
a second coupling end; and
a coupling element directly engaged with the first coupling end and the second coupling end, wherein the coupling element comprises a plurality of arm stabilization elements disposed around an inner portion of the coupling element, each of the plurality of arm stabilization elements configured to stabilize the first coupling end and the second coupling end in one of a plurality of different positions with respect to the coupling element.

21. The system of claim 20 wherein the system further comprises a third elongate member comprising
a third engaging end with a third hook element adapted to directly engage the lamina of the first vertebra,
a third coupling end directly engaged with the coupling element, and
a third length adjustment element disposed between the third engaging end and the third coupling end, wherein the third length adjustment element has a first configuration with a first length and a second configuration with a second length shorter than the first length
a fourth elongate member comprising
a fourth engaging end with a fourth hook element adapted to directly engage the lamina of the second vertebra and
a fourth coupling end directly engaged with the coupling element.

22. The system of claim 20 wherein the coupling element has a generally annular configuration and a first end and a second end, wherein the first and second ends define a discontinuity in the generally annular configuration.

23. A method of stabilizing at least two vertebrae, comprising:
directly engaging a first hooked end of a first elongate member with a lamina of a first vertebra;
directly engaging a first hooked end of a second elongate member with a lamina of a second vertebra, wherein a second end of the first elongate member and a second end of the second elongate member are each directly coupled to a coupling element in one of a plurality of different positions defined by a plurality of arm stabilization elements, at least one of the first and second elongate members comprising a plurality of bends aligned in the same plane;
positioning the coupling element in a position inferior to the lamina of the first vertebra and superior to the lamina of the second vertebra; and
reconfiguring the plurality of bends upon thermal activation, thereby reducing the length of at least one of the first elongate member and the second elongate member, thereby increasing the stability of the first vertebra relative to the second vertebra.

24. The method of claim 23 wherein reducing the length of at least one of the first elongate member and the second elongate member comprises reducing the length of the first elongate member and the second elongate member.

25. The method of claim 23 wherein reconfiguring the plurality of bend comprises reconfiguring the plurality of bends from a first configuration with a first length to a second memory configuration with a second length, wherein the second length is shorter than the first length.

26. The method of claim 23 further comprising directly engaging the second end of the first elongate member and the second end of the second elongate member with the coupling element.

27. The method of claim 23 wherein each of the second ends are directly coupled with an annular configuration of the coupling element.

* * * * *